United States Patent [19]

Tsuda et al.

[11] Patent Number: 4,822,780

[45] Date of Patent: Apr. 18, 1989

[54] CARBOXAMIDE COMPOUNDS

[75] Inventors: Yoshihiko Tsuda; Yoshiaki Tsuda, both of Tokushima, Japan

[73] Assignee: Otsuka Pharmaceutical Factory, Inc., Tokushima, Japan

[21] Appl. No.: 71,010

[22] Filed: Jul. 8, 1987

[51] Int. Cl.⁴ ........................ A01N 57/14; C07F 9/18

[52] U.S. Cl. .................................. 514/119; 558/191; 558/192; 558/190

[58] Field of Search ...................... 558/190, 191, 192; 514/119

[56] References Cited

U.S. PATENT DOCUMENTS

| | | | |
|---|---|---|---|
| 3,681,476 | 8/1972 | Gutman | 558/190 |
| 4,232,010 | 11/1980 | Tsukamoto et al. | 424/200 |
| 4,268,507 | 5/1981 | Mong | 424/217 |
| 4,309,364 | 1/1982 | Bentzen et al. | 260/931 |
| 4,371,527 | 2/1983 | Bentzen et al. | 424/204 |
| 4,416,877 | 11/1983 | Bentzen et al. | 424/204 |
| 4,626,528 | 12/1986 | McHenry | 558/190 |

FOREIGN PATENT DOCUMENTS 151199 7/1986 Japan .

OTHER PUBLICATIONS

Journal of American Chemical Society, vol. 95(7) p. 2362 (1973) and vol. 98(16) p. 4913 (1976).

*Primary Examiner*—H. M. S. Sneed
*Assistant Examiner*—Chung K. Pak
*Attorney, Agent, or Firm*—Sughrue, Mion, Zinn, Macpeak & Seas

[57] ABSTRACT

A carboxamide compound of the formula:

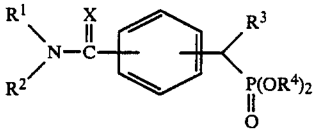

wherein $R^1$, $R^2$, $R^3$, $R^4$ and X are as defined and pharmaceutically acceptable salts thereof, and composition containing the compound are disclosed.

The compound is useful as a calcium antagonistic agent and an antiinflammatory agent.

6 Claims, No Drawings

CARBOXAMIDE COMPOUNDS

FIELD OF THE INVENTION

This invention relates to new carboxamide compounds and pharmaceutically acceptable salts thereof which are useful as calcium antagonistic agents and antiinflammatory agents and a pharmaceutical composition containing a carboxamide compound or a pharmaceutically acceptable salt thereof.

BACKGROUND OF THE INVENTION

Various carboxamide compounds having phosphonate group(s) are known as described in the Journal of the American Chemical Society Vol. 95(7) P2362(1973), and ibid, Vol. 98(16) P4913(1976), but it is not known that these compounds have a calcium antagoistic action and an antiinflammatory action.

Also, phosphonate compounds having activity as hypoglycemic and/or antiatherogenic agents are known as described in U.S. Pat. Nos. 4,268,507, 4,371,527 and 4,416,877, but the carboxamide compound of this invention is structurally different from them.

SUMMARY OF THE INVENTION

It is an object of the invention to provide a carboxamide compound having a calcium antagonistic action and an antiinflammatory action.

Another object of the invention is to provide a pharmaceutical composition containing an effective amount as a calcium antagonistic agent or an antiinflammatory agent of a carboxamide compound.

Still another object of the invention is to provide method of therapeutical treatment of the disease utilizing a calcium antagonistic action and an antiinflammatory action of a carboxamide compound by administering an effective amount of the compound.

This invention has been attained by the earnest studies of the inventors and in one aspect has been completed by providing a carboxamide compound represented by the following general formula [I] and pharmaceutically acceptable salts thereof:

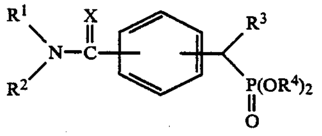

[I]

wherein $R^1$ and $R^2$ represent, respectively, a hydrogen atom, an alkyl group, a cycloalkyl group, a diphenyl lower alkyl group, or a group of the formula:

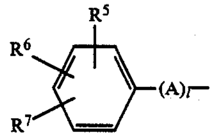

in which $R^5$, $R^6$ and $R^7$ represent, respectively, a hydrogen atom, a halogen atom, a nitro group, a lower alkoxy group, a lower alkoxycarbonyl group, a lower alkyl group, a halogen-substituted lower alkyl group, a cyano group, a carboxy group, or a hydroxy group; A represents a lower alkylene group; l represents 0 or 1; $R^1$ and $R^2$ together with the nitrogen atom bonding them may form a heterocyclic group which may contain additional hetero atom(s) consisting of a nitrogen atom and an oxygen atom, and the heterocyclic group may be substituted with a lower alkyl group, a phenyl lower alkyl group, or a phenyl group which may have a lower alkyl group, a lower alkoxy group, a halogen atom, or a halogen-substituted lower alkyl group as a substituent group; $R^3$ represents a hydrogen atom, an alkyl group, or a phenyl lower alkyl group; $R^4$ represents a lower alkyl group or a phenyl group; and X represents an oxygen atom or a sulfur atom.

In another aspect, the invention provides a pharmaceutical composition containing an effective amount as the calcium antagonistic agent or antiinflammatory agent of the compound represented by the formula [I] or a pharmaceutically acceptable salt thereof.

In still another aspect, the invention provides a method of therapeutical treatment of the disease utilizing the calcium antagonistic action and antiinflammatory action of the compound represented by the formula [I] by administrating an effective amount of the compound or a pharmaceutically acceptable salt thereof.

The compound according to the invention represented by the formula [I] has excellent calcium antagonistic action and antiinflammatory action. Therefore it is useful as a therapeutic and preventive agent against ischemic cardiac disease such as angina pectoris, myocardial infarct, and arrhythmia, and against hypertension, and an antiinflammatory agent. In addition it features in long duration of such medicinal action and low toxicity.

DETAILED DESCRIPTION OF THE INVENTION

The groups shown in the formula [I] are specifically exemplified as follows:

The term "alkyl" as used herein may include alkyl groups having 1 to 12 carbon atoms such as methyl, ethyl, propyl, isopropyl, butyl, tert-butyl, pentyl, hexyl, heptyl, octyl, nonyl, decyl, undecyl, dodecyl and the like.

The term "cycloalkyl" as used herein may include cycloalkyl groups having 3 to 8 carbon atoms such as cyclopropyl, cyclobutyl, cyclopentyl, cyclohexyl, cycloheptyl, cyclooctyl and the like.

The term "halogen atom" as used herein refers to an atom such as fluorine, chlorine, bromine, and iodine.

The term "lower alkoxy" as used herein may include alkoxy groups having 1 to 6 carbon atoms such as methoxy, ethoxy, propoxy, isopropoxy, butoxy, tert-butoxy, pentyloxy, hexyloxy and the like.

The term "lower alkoxycarbonyl" as used herein may include alkoxycarbonyl groups having 1 to 6 carbon atoms in the alkoxy moiety such as methoxycarbonyl, ethoxycarbonyl, propoxycarbonyl, isopropoxycarbonyl, butoxycarbonyl, tertbutoxycarbonyl, pentyloxycarbonyl, hexyloxycarbonyl and the like.

The term "lower alkyl" as used herein may include alkyl groups having 1 to 6 carbon atoms such as methyl, ethyl, propyl, isopropyl, butyl, tert-butyl, pentyl, hexyl and the like.

The term "halogen-substituted lower alkyl" as used herein may include alkyl groups having 1 to 6 carbon atoms and 1 to 3 l halogen atoms such as trifluoromethyl, trichloromethyl, 2,2,2-trifluoroethyl and the like.

The term "diphenyl lower alkyl" as used herein may include diphenyl alkyl groups having 1 to 6 carbon atoms in the alkyl moiety such as diphenylmethyl, 2,2-diphenylethyl, 3,3-diphenylpropyl, 4,4-diphenylbutyl and the like.

The term "phenyl lower alkyl" as used herein may include phenyl alkyl groups having 1 to 6 carbon atoms in the alkyl moiety such as benzyl, α-phenethyl, β-phenethyl, 3-phenylpropyl, 4-phenylbutyl, 2-methyl-2-phenylethyl, 2-methyl-3-phenylpropyl and the like.

The term "lower alkylene" as used herein may include alkylene groups having 1 to 6 carbon atoms such as methylene, ethylene, methylmethylene, 1-methylethylene, trimethylene, 2-methylpropylene, tetramethylene, pentamethylene, hexamethylene and the like.

The term "phenyl group which may have a lower alkyl group, a lower alkoxy group, a halogen atom, or a halogen-substituted lower alkyl group as a substituent group" as used herein may include phenyl groups which may have 1 to 3 substituents selected from the group consisting of a ($C_1$-$C_6$)-alkyl group, a ($C_1$-$C_6$)alkoxy group, a halogen atom and a ($C_1$-$C_6$)alkyl group substituted with 1 to 3 halogen atoms such as phenyl, 4-methylphenyl, 3-trifluoromethylphenyl, 3,4-dimethylphenyl, 3,4,5-trimethylphenyl, 2-ethylphenyl, 4-trichloromethylphenyl, 2-methoxyphenyl, 3,4-dimethoxyphenyl, 3,4,5-trimethoxyphenyl, 3-ethoxyphenyl, 4-methoxyphenyl, 4-chlorophenyl, 3,4-dichlorophenyl, 2,6-dichlorophenyl, 3,4,5-trichlorophenyl, 3,4-dibromophenyl, 4-fluorophenyl, 2-fluorophenyl, 2-chlorophenyl, 4-bromophenyl, 4-chloro-2-methylphenyl, 3,4-dimethoxy-2-chlorophenyl and the like.

The group of the formula:

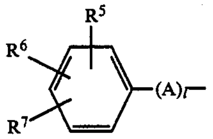

(where l is 0) may include, in addition to the phenyl group and substituted phenyl group mentioned above, 4-nitrophenyl, 2-nitrophenyl, 2-methoxycarbonylphenyl, 2-hydroxy-4-ethoxycarbonylphenyl, 4-cyanophenyl, 2-cyanophenyl, 2-carboxyphenyl, 2-hydroxyphenyl, 4-hydroxyphenyl, 2-hydroxy-4-methylphenyl, 4-methoxycarbonylphenyl and the like.

The group of the formula:

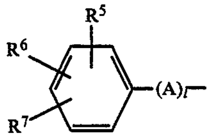

(where l is 1) may include benzyl, α-phenethyl, β-phenethyl, 3-phenylpropyl, 4-phenylbutyl, 4-methylbenzyl, 2,5-dimethylbenzyl, 3-trifluoromethylbenzyl, 2-ethylbenzyl, 4-trichloromethylbenzyl, α-(2-methoxyphenyl)ethyl, β-(3,4-dimethoxyphenyl)ethyl, 3-ethoxybenzyl, 4-methoxybenzyl, 4-chlorobenzyl, 2,4-dichlorobenzyl, β-(2,6-dichlorophenyl)ethyl, 3,4-dibromobenzyl, α-(4-fluorophenyl)ethyl, 2-fluorobenzyl, 2-chlorobenzyl, 3,4-dimethoxy-2-chlorobenzyl, 2-nitrobenzyl, 3-(4-nitrophenyl)propyl, 4-nitrobenzyl and the like.

The term "heterocyclic group formed of $R^1$ and $R^2$ together with the nitrogen atom bonding them, and which may contain additional hetero atom(s) consisting of a nitrogen atom and an oxygen atom" as used herein may include 1-pyrrolidinyl, piperidino, 1-piperazinyl, morpholino and the like.

The term "heterocyclic group which is substituted with a lower alkyl group, a phenyl lower alkyl group, or a phenyl group which may have a lower alkyl group, a lower alkoxy group, a halogen atom, or a halogen-substituted lower alkyl group as a substituent group" as used herein may include heterocyclic groups having a substituent selected from the group consisting of a ($C_1$-$C_6$)alkyl group, a phenyl-($C_1$-$C_6$)alkyl group and a phenyl group which may have 1 to 3 substituents selected from the group consisting of a ($C_1$-$C_6$)alkyl group, a ($C_1$-$C_6$)alkoxy group, a halogen atom and a ($C_1$-$C_6$)alkyl group having 1 to 3 halogen atoms such as 4-methyl-1-piperazinyl, 4-ethyl-1-piperazinyl, 4-tert-butyl-1-piperazinyl, 4-phenyl-1-piperazinyl, 4-benzyl-1-piperazinyl, 4-(2-methoxyphenyl)-1-piperazinyl, 4-(3-ethoxyphenyl)-1-piperazinyl, 4-(4-methoxyphenyl)-1-piperazinyl, 4-(4-chlorophenyl)-1-piperazinyl, 4-(2-fluorophenyl)-1-piperazinyl, 4-(4-bromophenyl)-1-piperazinyl, 4-(4-fluorophenyl)-1-piperazinyl, 4-(2-methylphenyl)-1-piperazinyl, 4-(4-etlylphenyl)-1-piperazinyl, 4-(3-trifluorophenyl)-1-piperazinyl, 4-(β-phenethyl)-1-piperazinyl, 4-methylpiperidino, 4-phenylpiperidino, 4-(3-trifluoromethylphenyl)-1-piperazinyl, 4-(4-chlorophenyl)-1-piperazinyl and the like.

The compound according to the invention can be manufactured by various methods. The typical methods are shown by the following Reaction Schemes 1-6:

Reaction Scheme-1

A method in which a carboxylic acid derivative [II] is reacted with an amine [III].

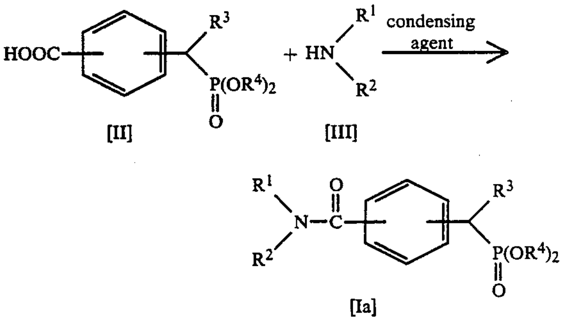

[II] [III]

[Ia]

Reaction Scheme-2

A method in which a carboxylic acid derivative [II] in the form of mixed anhydride is reacted with an amine [III].

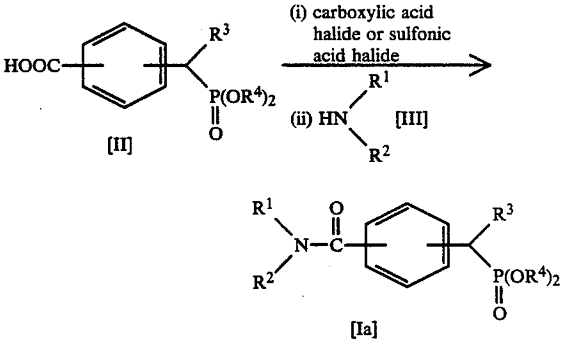

[II] [III]

[Ia]

Reaction Scheme-3

A method in which a carboxamide derivative having a halogen atom [VI] is reacted with a phosphite [V].

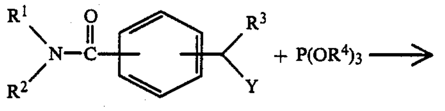

[IV] [V]

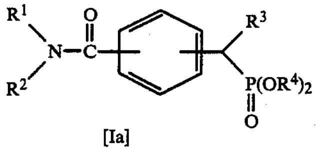

[Ia]

Reaction Scheme-4

A method in which a carboxamide derivative [Ib] is reacted with an alkyl halide [VI] in the presence of a base.

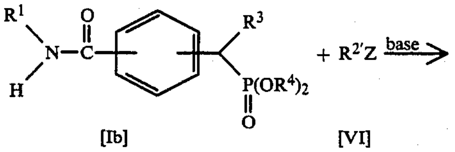

[Ib] [VI]

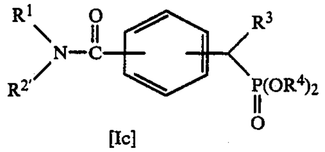

[Ic]

Reaction Scheme-5

A method in which a carboxamide derivative [Ia] is reacted with phosphorus pentasulfide [VII].

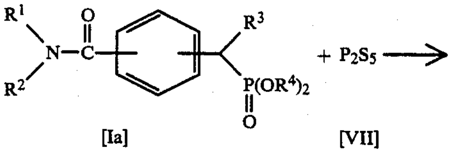

[Ia] [VII]

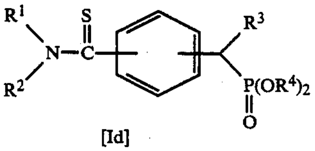

[Id]

Reaction Scheme-6

A method in which an ester [Ie] is hydrolyzed with a base.

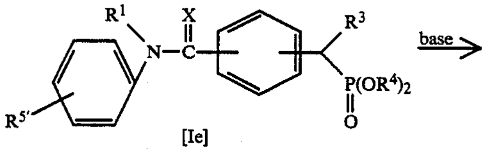

[Ie]

-continued

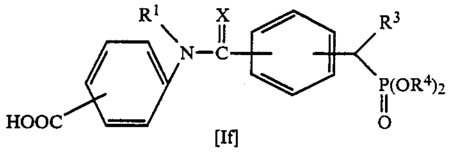

[If]

In the Reaction Schemes 1 to 6, $R^1$ to $R^4$ and X have the same meanings as defined before. Y and Z represent halogen atoms, $R^{2'}$ represents $R^2$ excluding a hydrogen atom, and $R^{5'}$ represents a lower alkoxycarbonyl group.

The condensing agents to be used in the reaction of Reaction Scheme 1 are those conventionally well known, such as N,N'-dicyclohexylcarbodiimide, 1-hydroxybenzotriazole, N-hydroxysuccinimide, diethyl phosphorocyanidate, diphenyl phosphoroazidate and the like. Among these, the use of diethyl phosphorocyanidate together with triethylamine is preferable. The reaction is conducted in a known aprotic solvent, preferably in N,N-dimethylformamide (DMF) at a temperature range of nearly ice-cooled to room temperature for about 0.5 to 2 hours. Proportion of the compound [II] to the compound [III] is not limited and can be varid widely. But usually, in a range from an equimolar amount to an excess, preferable an equimolar amount, of the compound [III] per mol of the compound [II] is used. The condensing agent, particularly diethyl phosphorocyanidate and triethylamine, is used in a range from an equimolar amount to an excess, preferably in a small excess per mol of the compound [II].

The reaction through the mixed acid anhydride shown in Reaction Scheme 2 is generally conducted by use of carboxylic acid halides or sulfonic acid halides which can form a mixed acid anhydride in the presence of a basic compound. The carboxylic acid halides or sulfonic acid halides usable in the reaction are usually, for example, ethyl chlorocarbonate, isobutyl chlorocarbonate, p-toluenesulfonyl chloride, benzenesulfonyl chloride and the like. Among these, preferable is ethyl chlorocarbonate. As for the basic compound, any of known ones which do not affect the reaction can be used, and preferably tertiary amines such as triethylamine, pyridine, diethylaniline, and N-methylmorpholine are used. The reaction is conducted in an adequate solvent. Examples of the solvent as used include aromatic or aliphatic hydrocarbons such as benzene, toluene, xylene, petroleum ether, etc., acyclic or cyclic ether such as diethyl ether, dimethoxyethane, tetrahydrofuran (THF), dioxane, etc., ketones such as acetone, methylethyl ketone, acetophenone, etc., halogenated hydrocarbons such as chloroform, carbon tetrachloride, 1,2-dichloroethane etc., and the like. The proportion of the compound [II] to the compound [III] is not limited, but it is preferable to use the compound [III] in an equimolar amount to in an excess per mol of the compound [II]. The carboxylic acid halides or sulfuric acid halides and the basic compound are used preferably in an equimolar amount to a small excess mol on the basis of the compound [II]. The reaction proceeds in any condition of cooling, room temperature, or heating, but usually it is preferable to use a range from room temperature to the reflux temperature of the solvent. The reaction is completed in about 0.5 to 5 hours.

The reaction shown in Reaction Scheme 3 can be carried out in a solvent which does not affect the reaction such as lower alcoholes, aromatic or aliphatic hydrocarbons, and DMF, but is preferably carried out without solvent. The compound [V] is usually in an excess over the compound [IV]. The reaction temperature is about 130° to 180° C., preferably about 140° to 150° C., the reaction time, though different depending upon the type of the compound [V], is usually about 0.5 to 3 hours.

As the base used in Reaction Scheme 4, known basic compounds in a wide range can be used. The typical examples are inorganic bases such as sodium carbonate, potassium carbonate, lithium hydroxide, sodium hydroxide, potassium hydroxide, sodium hydride, potassium hydride, sodium methoxide, potassium methoxide, sodium ethoxide, potassium ethoxide and the like. Among these, metal hydrides such as sodium hydride and potassium hydride are favorable. The reaction is usually conducted in an adequate solvent. Examples of the solvent include for example, aromatic or aliphatic hydrocarbons such as benzene, toluene, xylene, peteroleum ether, etc., acyclic or cyclic ethers such as diethyl ether, methyl phenyl ether, THF, dioxane, etc., lower alcohols such as methanol, ethanol, isopropanol etc. are used adequately selected according to the type of base used, properties of the raw material, and other reaction conditions. The proportion of the compound [Ib] to the compound [VI] in the reaction is not limited, but usually the compound [VI] is used in an equimolar amount to in an excess, preferably an equimolar amount, per mol of the compound [Ib]. The proportion of the base is preferably an equimolar amount to a small excess per mol of the compound [Ib]. The reaction proceeds at any condition of cooling, room temperature, or heating, but preferably in the range of room temperature to the reflux temperature of the solvent. The reaction is completed generally in 1 to 6 hours.

In the reaction shown in Reaction Scheme 5, the proportion of the compound [Ia] to phosphorus pentasulfide [VII] is not particularly limited and can be selected in a wide range. But usually the compound [VII] is used in an equimolar amount to in an excess, preferably in 1.5 to 2.5 mols, per mol of the compound [Ib]. The compound [Ia] as a starting compound can be obtained by the method shown in Reaction Scheme of 1, 2, 3, or 4. The reaction generally proceeds favorably in an aprotic solvent. Examples of the solvent include tertiary amines such as pyridine, triethylamine, dimethylaniline, etc., aromatic hydrocarbons such as benzene, toluene, xylene, etc., acetonitril and the like. Preferably, a mixed solvent of benzene and pyridine can be used. The mixing ratio is not particularly limited, but preferably benzene and pyridine are present in a ratio (volume) of 4:1 to 5:1. The reaction temperature is usually in a range from room temperature to the reflux temperature of the solvent, preferably in a range of 70° to 90° C., and the reaction is completed in about 2 to 10 hours.

As to the carboxamide derivative according to the invention, when $R^2$ of the compound [If] is the group of the formula:

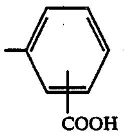

the compound can be prepared by hydrolyzing with a base the compound [Ie], where $R^2$ thereof is the group of the formula:

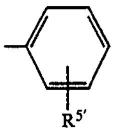

(Wherein $R^{5'}$ has the same meaning as defined before), according to the method shown in Reaction Scheme 6. The compound [Ie] can be obtained by the method shown in one of Reaction Schemes 1 to 5. Examples of the base used in the hydrolysis reactions include alkali metal hydroxides such as lithium hydroxide, sodium hydroxide, potassium hydroxide and the like. The base is usually used in an excess amount over the compound [Ie]. The reaction is conducted in a solvent, for example, a mixture of lower alcohol such as methanol, ethanol, isopropanol etc., with water, in cooling, at room temperature, or in heating, preferably at room temperature, for about 2 to 10 hours.

The thus obtained compounds according to the invention can be easily isolated and purified by ordinary separating means such as solvent extraction, distillation, recrystallization, column chromatography, preparative thin-layer chromatography and the like.

The compounds according to the invention can be used as the effective ingredient in the unmodified form or together with a preparative carrier of ordinary use, and can be administered to man and animal as medicines such as anti-hypertensive agent. The unit form of dose is not limited and various known forms can be selected as required. Such unit forms of dose are, for example, oral agents such as tablets, powder, granules, and oral solution, and non-oral agents such as injection agent. The amount of effective ingredient to be dosed is not particularly limited and can be selected from a wide range, but to attain expected effect, usually about 0.05 to 100 mg per 1 kg of the weight of the patient per day is preferable. In a unit form of dose, about 1 to 500 mg of the effective ingredient is generally contained.

A preparation containing the compound according to the invention as an active ingredient is manufactured by a conventional procedure. For example, tablets are manufactured by mixing the compound according to the invention with a pharmaceutically acceptable vehicle such as gelatine, starch, lactose, magnesium stearate, talc, and gum arabic. Capsules are made, after mixing the compound of the invention with an inactive pharmaceutical filler or diluent, by filling rigid gelatine capsules or soft gelatine capsules, etc. with the mixture. Syrup agents or elixiria agents are manufactured by mixing the compound of the invention with a sweetness agent such as sucrose, an antiseptic such as methylparaben and propylparaben, a coloring agent, and a flavoring material. Non-oral medicines are manufactured by dissolving the compound of the invention in a sterilized liquid carrier. A preferable liquid carrier is physiological saline solution or alcohols such as ethyl alcohol. A liquid agent having desirable transparency, stability, and adaptability to non-oral use is manufactured by dissolving about 1 to 500 mg of the active ingredient in physiological saline solution and an organic solvent, and dissolving in polyethylene glycol having a molecular weight of 200 to 5000. Such liquid agents preferably contain a wetting agent such as sodium carboxymethyl cellulose, methyl cellulose, polyvinyl pyrrolidone, and polyvinyl alcohol. The liquid agent may further contain, a microbicide or fungicide such as benzyl alcohol, phenol, and thimerosal, an isotonic agent such as sucrose and sodium chloride, a stabilizer, and a buffering agent, as required. The non-oral medicines may be frozen after filling to increase stability and can remove water by the lyophilization technique known in the field. And the freeze-dried powder can be reprepared by the addition of water immediately before use.

Hereinafter, this invention will be described in greater detail with reference to Examples, Pharmacological study and Pharmaceutical Examples

EXAMPLES

Example 1

To a solution of 1.36 g of 4-diethoxyphosphinylmethylbenzoic acid and 0.54 g of benzylamine in 15 ml of dry DMF was added dropwise a solution of 1.00 g of diethyl phosphorocyanidate in 2 ml of dry DMF under ice-cooling with stirring. Then, a solution of 0.56 g of triethylamine in 3 ml of dry DMF was added dropwise thereto requiring 5 minutes. The mixture was stirred for 30 minutes under ice-cooling and one hour at room temperature. After adding 30 ml of water, the reaction mixture was extracted with ethyl acetate, and the organic layer was washed with water two times. After drying over anhydrous sodium sulfate, the solvent was evaporated. The residue was subjected to silica gel column chromatography (eluent; chloroform:ethyl acetate=1:1), and 4-diethoxyphosphinylmethyl-N-benzylbenzamide was obtained. It was recrystallized from benzene-n-hexane to give 1.60 g of colorless needles.

m.p.: 99°–100° C.

EXAMPLES 2 TO 34

In the same manner as in Example 1 and using adequate starting materials, the compounds as shown in Table 1 were obtained. When the product is an oily substance, in the column of melting point in Table 1, the analyses (γ value: ppm) of $^1$H-NMR ($CDCl_3$, internal standard TMS) are described. (Same as in the following Tables.)

TABLE 1

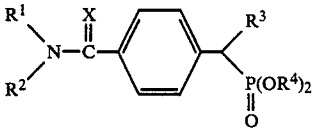

| Example No. | $R^1$ | $R^2$ | $R^3$ | $R^4$ | X | Melting point (°C.) (recrystallization solvent) |
|---|---|---|---|---|---|---|
| 2 | $CH_3$ | H | H | $CH_2CH_3$ | O | 121.5–122.5 (benzene-n-hexane) |
| 3 | $H_3C(CH_2)_4CH_2$ | H | $CH_3$ | $CH_2CH_3$ | O | 0.89 (t, J=5.8Hz, 3H), 1.1–1.9 (m, 8H), 1.16 (t, J=7.0Hz, 3H), 1.28 (t, J=7.0Hz, 3H), 1.58 (dd, J=18.2, 7.5Hz, 3H), 2.9–3.6 (m, 3H), 3.6–4.3 (m, 4H), 6.3 (br, t, 1H), 7.40 (dABq, J=2.4, 7.9Hz, 2H), 7.73 (ABq, J=7.9Hz, 2H) |
| 4 | 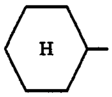 | H | H | $CH_2CH_3$ | O | 146.5–147.5 (benzene-n-hexane) |
| 5 | 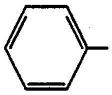 | H | H | $CH_2CH_3$ | O | 139.5–140.5 (benzene-n-hexane) |
| 6 | 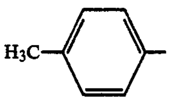 | H | H | $CH_2CH_3$ | O | 157.5–158.5 (benzene-n-hexane) |
| 7 | 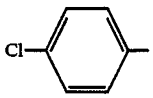 | H | H | $CH_2CH_3$ | O | 144.5–145.5(decomposition) (benzene-n-hexane) |
| 8 | 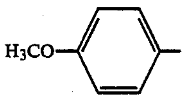 | H | H | $CH_2CH_3$ | O | 131.5–132.5 (benzene-n-hexane) |

TABLE 1-continued

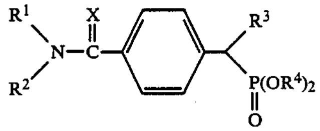

| Example No. | $R^1$ | $R^2$ | $R^3$ | $R^4$ | X | Melting point (°C.) (recrystallization solvent) |
|---|---|---|---|---|---|---|
| 9 | 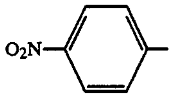 | H | H | $CH_2CH_3$ | O | 206.5–207.5 (chloroform-benzene) |
| 10 | 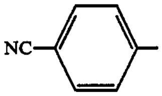 | H | H | $CH_2CH_3$ | O | 177–178 (chloroform-benzene) |
| 11 | 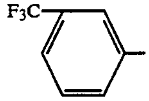 | H | H | $CH_2CH_3$ | O | 145–146 (benzene-n-hexane) |
| 12 | 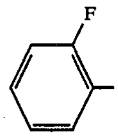 | H | H | $CH_2CH_3$ | O | 109–110 (benzene-n-hexane) |
| 13 | 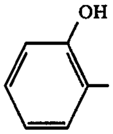 | H | H | $CH_2CH_3$ | O | 137.5–138.5 (benzene-n-hexane) |
| 14 | 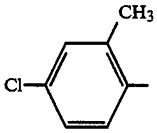 | H | H | $CH_2CH_3$ | O | 147–148 (benzene-n-hexane) |
| 15 | 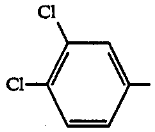 | H | H | $CH_2CH_3$ | O | 169.5–170.5 (benzene-n-hexane) |
| 16 | 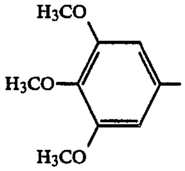 | H | H | $CH_2CH_3$ | O | 125–126 (benzene-n-hexane) |
| 17 | 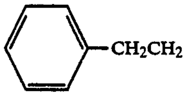 | H | H | 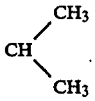 | O | 115.5–116.5 (benzene-n-hexane) |
| 18 | 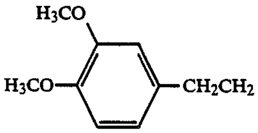 | H | H | $CH_2CH_3$ | O | 1.24 (t, J=7.0Hz, 6H), 2.87 (t, J=7.0Hz, 2H), 3.17 (d, J=22.0Hz, 2H), 3.5–3.9 (m, 2H), 3.84 (s, 3H), 3.86 (s, 3H), 3.8–4.2 (m, 4H), 6.3 (br. t, 1H), 6.7–6.9 (m, 3H), 7.33 (dABq, J=2.2, 8.3Hz, 2H), 7.66 (ABq, J=8.3Hz, 2H) |

TABLE 1-continued

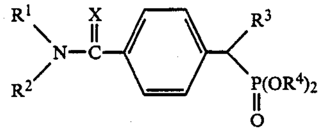

| Example No. | $R^1$ | $R^2$ | $R^3$ | $R^4$ | X | Melting point (°C.) (recrystallization solvent) |
|---|---|---|---|---|---|---|
| 19 | $CH_2CH_3$ | $CH_2CH_3$ | H | $CH_2CH_3$ | O | 1.2 (br. t, 6H), 1.25 (t, J=7.0Hz, 6H), 3.1-3.8 (m, 4H), 3.16 (d, J=21.8Hz, 2H), 3.8-4.2 (m, 4H), 7.33 (s, 4H) |
| 20 | 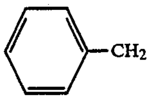 | $CH_3$ | H | $CH_2CH_3$ | O | 1.23 (t, J=7.0Hz, 6H), 2.9 (br. s, 3H), 3.16 (d, J=22.0Hz, 2H), 3.8-4.2 (m, 4H), 4.5, 4.7 (each br. s, totally 2H), 7.0-7.6 (m, 9H) |
| 21 | 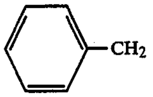 | 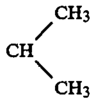 | H | $CH_2CH_3$ | O | 98.5-99.5(decomposition) (benzene-n-hexane) |
| 22 | 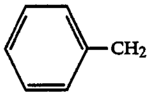 | 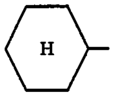 | H | $CH_2CH_3$ | O | 89.5-90.5(decomposition) (benzene-n-hexane) |
| 23 | 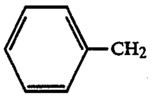 | 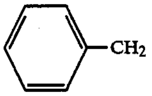 | H | $CH_2CH_3$ | O | 1.21 (t, J=7.0Hz, 6H), 3.15 (d, J=22.4Hz, 2H), 3.8-4.2 (m, 4H), 4.4 (br. s, 2H), 4.7 (br. s, 2H), 7.0-7.6 (m, 14H) |
| 24 | 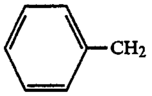 | 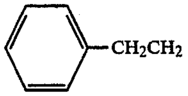 | $CH_3$ | $CH_2CH_3$ | O | 1.11 (t, J=7.0Hz, 3H), 1.25 (t, J=7.0Hz, 3H), 1.56 (dd, J=18.5, 7.5 Hz, 3H), 2.5-5.0 (m, 11H), 6.6-7.6 (m, 14 H) |
| 25 | $-CH_2(CH_2)_2CH_2-$ | | $CH_3$ | $CH_2CH_3$ | O | 1.16 (t, J=7.0Hz, 3H), 1.28 (t, J=7.0Hz, 3H), 1.58 (dd, J=18.5, 7.5 Hz, 3H), 1.6-2.2 (m, 4H), 2.9-4.2 (m, 9H), 7.38 (dABq, J=2.0 8.6Hz, 2H), 7.48(ABq, J=8.6Hz, 2H) |
| 26 | $-CH_2(CH_2)_3CH_2-$ | | H | $CH_2CH_3$ | O | 1.25 (t, J=7.0Hz, 6H), 1.3-1.9 (m, 6H), 3.1-3.9 (m, 4H), 3.16 (d, J=21.8Hz, 2H), 3.8-4.2 (m, 4H), 7.34 (s, 4H) |
| 27 | $-CH_2NHCH_2CH_2-$ | | H | $CH_2CH_3$ | O | 1.26 (t, J=7.0Hz, 6H), 2.6-2.9 (m, 4H), 3.17 (d, J=21.8Hz, 2H), 3.2-3.9 (m, 4H), 3.9-4.2 (m, 4H), 7.35 (s, 4H) |
| 28 | $-CH_2CH_2NCH_2CH_2-$<br>\|<br>$CH_3$ | | H | $CH_2CH_3$ | O | 1.26 (t, J=7.0Hz, 6H), 2.2-2.6 (m, 4H), 2.32 (s, 3H), 3.17 (d, J=22.0Hz, 2H), 3.3-3.9 (m, 4H), 3.9-4.3 (m, 4H), 7.36 (s, 4H) |

TABLE 1-continued

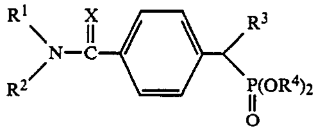

| Example No. | $R^1$ | $R^2$ | $R^3$ | $R^4$ | X | Melting point (°C.) (recrystallization solvent) |
|---|---|---|---|---|---|---|
| 29 | $-CH_2CH_2NCH_2-$ 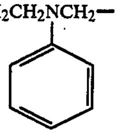 | | H | $CH_2CH_3$ | O | 1.26 (t, J=6.8Hz, 3H), 1.27 (t, J=6.8Hz, 3H), 2.9-3.3 (m, 4H), 3.17 (d, J=21.8Hz, 2H), 3.4-3.9 (m, 4H), 3.8-4.2 (m, 4H), 6.8-7.4 (m, 9H) |
| 30 | $-CH_2CH_2NCH_2CH_2-$ 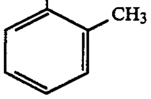 | | H | $CH_2CH_3$ | O | 87-89(decomposition) (benzene-n-hexane) |
| 31 | $-CH_2CH_2NCH_2CH_2-$ 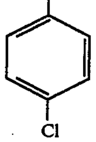 | | H | $CH_2CH_3$ | O | 137.5-138.5 (benzene-n-hexane) |
| 32 | $-CH_2CH_2NCH_2CH_2-$ 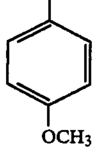 | | H | $CH_2CH_3$ | O | 92.0-93.5(decomposition) (benzene-n-hexane) |
| 33 | $-CH_2CH_2NCH_2-$ 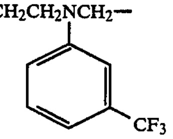 | | H | $CH_2CH_3$ | O | 108.5-109.5 (benzene-n-hexane) |
| 34 | $-CH_2CH_2NCH_2CH_2-$ 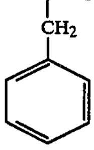 | | H | 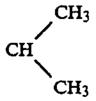 | O | 1.17 (d, J=6.2Hz, 6H), 1.27 (d, J=6.2Hz, 6H), 2.2-2.7 (m, 4H), 3.11 (d, J=21.8Hz, 2H), 3.2-4.1 (m, 4H), 3.54 (s, 2H), 4.4-4.9 (m, 2H), 7.1-7.6 (m, 9H) |

Example 35

To a solution of 0.73 g of 4-diethoxyphosphinylmethyl-N-(2-methoxycarbonylphenyl)benzamide in 10 ml of ethanol was slowly added 10 ml of 1N sodium hydroxide under ice-cooling with stirring. After stirring for 5 hours at room temperature, 10 ml of 2N hydrochloric acid was added thereto, and the mixture was extracted with chloroform. The extract was dried over anhydrous sodium sulfate, and the solvent was evaporated. The crystalline residue was recrystallized from benzene to give 0.60 g of colorless plate crystal of 4-diethoxyphosphinylmethyl-N-(2-carboxyphenyl)benzamide. mp: 171°-172° C.

EXAMPLE 36

To a solution of 1.36 g of 4-diethoxyphosphinylmethylbenzoic acid and 0.56 g of triethylamine in 15 ml of dry THF was slowly added a solution of 0.60 g of ethyl chlorocarbonate in 2 ml of dry THF under ice-cooling with stirring. After stirring for 30 minutes under ice-cooling, ammonia gas was slowly bubbled into the mixture for 15 minutes, stirred for 2 hours at room temperature. After adding 30 ml of water, the reaction mixture was extracted with chloroform. The extract was dried over anhydrous sodium sulfate and the solvent was evaporated. The residue was subjected to silica gel column chromatography (eluent; chloroform:methanol=10:1) to give 4-diethoxyphosphinylmethylbenzamide. it was recrystallized from chloroform-benzene mixture to give 0.80 g of colorless plate crystals. mp: 177.0°-177.5° C.

Examples 37 and 38

Except that instead of the ammonia gas, 3,3-diphenylpropylamine (Example 37) or morpholine (Example 38) was used, in the same manner as Example 35, compounds shown in Table 2 were obtained using adequate starting materials.

TABLE 2

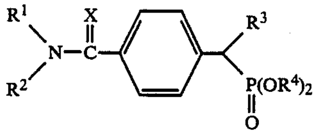

| Example No. | $R^1$ | $R^2$ | $R^3$ | $R^4$ | X | Melting point (°C.) (recrystallization solvent) |
|---|---|---|---|---|---|---|
| 37 | 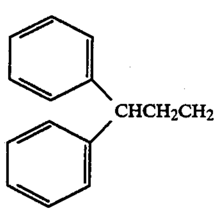 | H | H | $CH_2CH_3$ | O | 1.21(t, J=7.0Hz, 6H), 2.40(t, J=6.6Hz, 2H), 3.13(d, J=22.0Hz, 2H), 3.2-3.5(m, 2H), 3.8-4.1(m, 5H), 6.6(br. t, 1H), 7.1-7.7(m, 14H) |
| 38 | $-CH_2CH_2OCH_2CH_2-$ | | H | $CH_2CH_3$ | O | 89-91 (decomposition) (benzene-n-hexane) |

Example 39

A suspension of 1.07 g of 4-bromoethyl-N-(2-methoxycarbonylphenyl)benzamide in 5 ml of triethyl phosphite was stirred under heating at 140° to 150° C. for 30 minutes. After excess triethyl phosphite had been distilled off in vacuo, the residue was subjected to silica gel column chromatography (eluent; chloroform:methanol=1:1) to give 4-diethoxyphosphinylmethyl-N-(2-methoxycarbonylphenyl)benzamide. It was recrystallized from a benzene-n-hexane mixture to give 1.20 g of colorless needles.

mp: 111.5°-112.5° C.

Examples 40 to 48

In the same manner as Example 39 and using adequate starting materials, the compounds shown in the following Table 3 were obtained.

TABLE 3

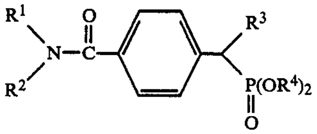

| Example No. | $R^1$ | $R^2$ | $R^3$ | $R^4$ | X | Melting point (°C.) (recrystallization solvent) |
|---|---|---|---|---|---|---|
| 40 | 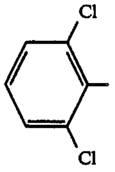 | H | H | 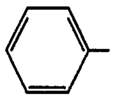 | O | 173.5-174.5 (benzene-n-hexane) |
| 41 | 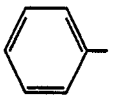 | $CH_3$ | H | $CH_2CH_3$ | O | 66.6-67.5 (ether-n-hexane) |
| 42 | 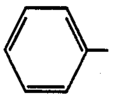 | 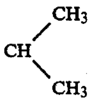 | H | $CH_2CH_3$ | O | 87.5-88.5 (benzene-n-hexane) |
| 43 | 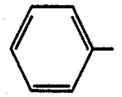 | 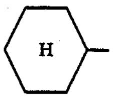 | H | $CH_2CH_3$ | O | 82-83 (benzene-n-hexane) |

TABLE 3-continued

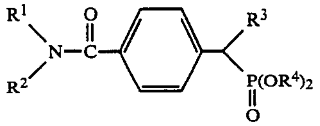

| Example No. | $R^1$ | $R^2$ | $R^3$ | $R^4$ | X | Melting point (°C.) (recrystallization solvent) |
|---|---|---|---|---|---|---|
| 44 | 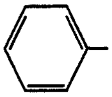 | 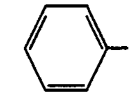 | H | $CH_2CH_3$ | O | 114.5–115.5 (benzene-n-hexane) |
| 45 | 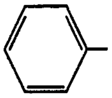 | 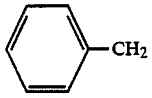 | H | $CH_2CH_3$ | O | 1.16(t, J=7.1Hz, 6H), 3.04(d, 22.0Hz, 2H), 3.7–4.1(m, 4H), 5.11(s, 2H), 6.8–7.4(m, 14H) |
| 46 | 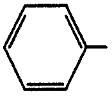 | 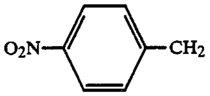 | H | $CH_2CH_3$ | O | 1.16(t, J=7.0Hz, 6H), 3.05(d, J=21.8Hz, 2H), 3.7–4.1(m, 4H), 5.21(s, 2H), 6.7–7.6(m, 11H), 8.0–8.2(m, 2H) |
| 47 | 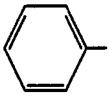 | 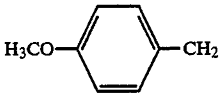 | H | $CH_2CH_3$ | O | 1.16(t, J=7.0Hz, 6H), 3.03(d, J=21.8Hz, 2H), 3.7–4.1(m, 4H), 3.77(s, 3H), 5.04(s, 2H), 6.6–7.4(m, 13H) |
| 48 | 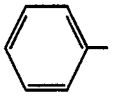 | 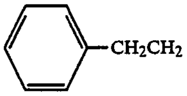 | H | $CH_2CH_3$ | O | 1.16(t, J=7.0Hz, 3H), 1.17(t, J=7.0Hz, 3H), 2.9–3.2(m, 2H), 3.04(d, J=22.0Hz, 2H), 3.7–4.3(m, 6H), 6.8–7.4(m, 14H) |

Example 49

To a solution of 0.50 g of 4-diethoxyphosphinylmethyl-N-(4-chlorophenyl)benzamide in 10 ml of dry THF was added in portions 0.07 g of sodium hydride (60%, in oil) under ice-cooling with stirring. After stirring for 30 minutes under ice cooling, a solution of 0.23 g of benzyl bromide in 2 ml of dry THF was added. After stirring for 5 hours at room temperature, 30 ml of water was added to the reaction mixture, and the mixture was extracted with chloroform. The extract was dried over anhydrous sodium sulfate, and the solvent was evaporated. The residue was subjected to silica gel column chromatography (eluent; chloroform:ethyl acetate=1:1) to give 4-diethoxyphosphinylmethyl-N-benzyl-N-(4-chlorophenyl)benzamide. It was recrystallized from benzene-n-hexane to give 0.40 g of colorless columnar crystals.

mp: 81°–82° C.

Eamples 50 to 64

In the same manner as Example 49 and using adequate starting materials, the compounds shown in the following Table 4 were obtained.

TABLE 4

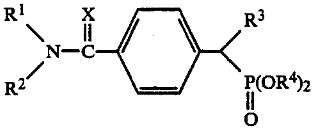

| Example No. | $R^1$ | $R^2$ | $R^3$ | $R^4$ | X | Melting point (°C.) (recrystallization solvent) |
|---|---|---|---|---|---|---|
| 50 | 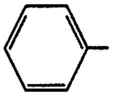 | $H_3C(CH_2)_6CH_2$ | H | $CH_2CH_3$ | O | 0.9(br.t, 3H), 1.17 (t, J=7.2Hz, 6H), 1.0–1.9(m, 12H), 3.04(d, J=21.5Hz, 2H), 3.6–4.2(m, 6H), 6.8–7.4(m, 9H) |

TABLE 4-continued

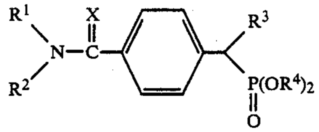

| Example No. | $R^1$ | $R^2$ | $R^3$ | $R^4$ | X | Melting point (°C.) (recrystallization solvent) |
|---|---|---|---|---|---|---|
| 51 | 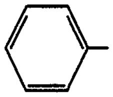 | $H_3C(CH_2)_6CH_2$ | $H_3C(CH_2)_6CH_2$ | $CH_2CH_3$ | O | 0.8-1.8(m, 26H), 0.86(t, J=7.2Hz, 3H), 1.02(t, J=7.2Hz, 3H), 1.23(t, J=7.2Hz, 6H), 2.6-3.2(m, 1H), 3.3-4.2(m, 6H), 6.8-7.3 (m, 9H) |
| 52 | 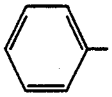 | 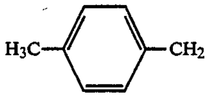 | H | $CH_2CH_3$ | O | 1.16(t, J=7.0Hz, 3H), 1.17(t, J=7.0Hz, 3H), 2.30(s, 3H), 3.03, 3.05(each d, J=22.0 Hz, totally 2H), 3.6-4.2(m, 4H), 5.03, 5.06(each s, totally 2H), 6.6-7.4 (m, 13H) |
| 53 | 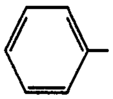 | 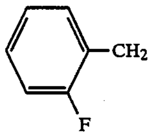 | H | $CH_2CH_3$ | O | 1.16(t, J=7.0Hz, 3H), 1.18(t, J=7.0Hz, 3H), 3.04, 3.06(each d, J=22.0Hz, totally 2H), 3.6-4.2(m, 4H), 5.16, 5.19(each s, totally 2H), 6.6-7.6(m, 13H) |
| 54 | 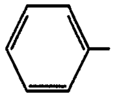 | 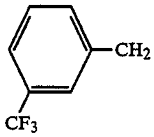 | H | $CH_2CH_3$ | O | 1.16(t, J=7.0Hz, 6H), 3.04(d, J=22.0Hz, 2H), 3.6-4.2(m, 4H), 5.15(s, 2H), 6.7-7.7(m, 13H) |
| 55 | 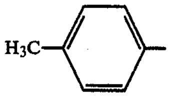 | 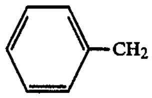 | H | $CH_2CH_3$ | O | 1.16(t, J=7.0Hz, 6H), 2.20(s, 3H), 3.04 (d, J=22.0Hz, 2H), 3.7-4.1(m, 4H), 5.08(s, 2H), 6.6-7.4(m, 13H) |
| 56 | 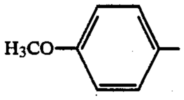 | 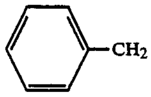 | H | $CH_2CH_3$ | O | 1.15(t, J=7.0Hz, 6H), 3.03(d, J=21.8Hz, 2H), 3.6-4.2(m, 4H), 3.66(s, 3H), 5.05(s, 2H), 6.5-7.4(m, 13H) |
| 57 | 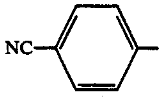 | 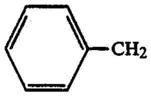 | H | $CH_2CH_3$ | O | 117-119 (benzene-n-hexane) |
| 58 | 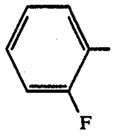 | 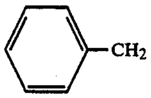 | H | $CH_2CH_3$ | O | 1.15(t, J=7.0Hz, 6H), 3.04(d, J=22.0Hz, 2H), 3.6-4.1(m, 4H), 4.8, 5.3(each br. s, totally 2H), 6.6-7.4(m, 13H) |

TABLE 4-continued

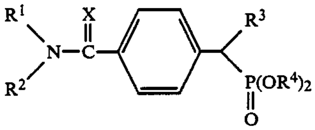

| Example No. | $R^1$ | $R^2$ | $R^3$ | $R^4$ | X | Melting point (°C.) (recrystallization solvent) |
|---|---|---|---|---|---|---|
| 59 | 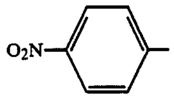 | 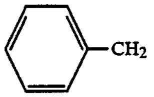 | H | $CH_2CH_3$ | O | 1.17(t, J=7.0Hz, 6H), 3.07(d, J=22.0Hz, 2H), 3.7-4.2(m, 4H), 5.19(s, 2H), 6.9-7.4(m, 11H), 7.9-8.1(m, 2H) |
| 60 | 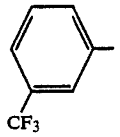 | 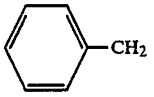 | H | $CH_2CH_3$ | O | 1.17(t, J=7.0Hz, 6H), 3.05(d, J=22.0Hz, 2H), 3.7-4.2(m, 4H), 5.13(s, 2H), 6.9-7.5(m, 13H) |
| 61 | 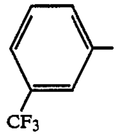 | 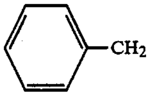 | 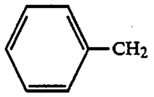 | $CH_2CH_3$ | O | 1.04(t, J=7.0Hz, 3H), 1.23(t, J=7.0Hz, 3H), 2.8-4.2(m, 7H), 5.10 (s, 2H), 6.7-7.5(m, 18H) |
| 62 | 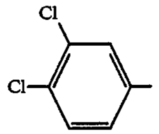 | 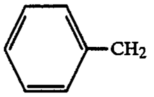 | H | $CH_2CH_3$ | O | 97-98* (benzene-n-hexane) |
| 63 | 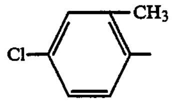 | 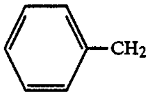 | H | $CH_2CH_3$ | O | 1.14(t, J=7.0Hz, 3H), 1.16(t, J=7.0Hz, 3H), 1.87(s, 3H), 3.03(d, J=21.8Hz, 2H), 3.6-4.2(m, 4H), 4.64, 5.28 (ABq, J=13.9Hz, 2H), 6.6-7.4(m, 12H) |
| 64 | 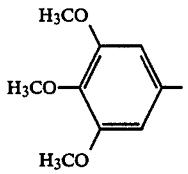 | 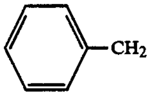 | H | $CH_2CH_3$ | O | 1.18(t, J=7.0Hz, 6H), 3.07(d, J=22.0Hz, 2H), 3.54(s, 6H), 3.7-4.2 (m, 4H), 3.74(s, 3H), 5.07(s, 2H), 6.06(s, 2H), 6.9-7.5(m, 9H) |

*The 1H-NMR spectrum of the compound of Example 62 is as follows:
δppm = 1.18(t, J=7.0Hz, 6H), 3.08(d, J=22.0Hz, 2H), 3.7-4.2(m, 4H), 5.08(s, 2H), 6.6-7.4(m, 12H)

Example 65

A suspension of 0.40 g of 4-diethoxyphosphinylmethyl-N-methyl-N-phenylbenzamide and 0.56 g of phosphorus pentasulfide in a mixed solvent of 20 ml of dry benzene and 5 ml of dry pyridine was refluxed for 7 hours. After being allowed to cool to room temperature, the reaction mixture was poured into 50 ml of ice water. The water layer was made acidic with 4N hydrochloric acid and extracted with chloroform. The extract was dried over anhydrous sodium sulfate, and the solvent was evaporated. The residue was subjected to silica gel column chromatography (eluent; benzene:ethyl acetate=1:1) to give 4-diethoxyphosphinylmethyl-N-methyl-N-phenylthiobenzamide. Recrystallization from benzene-n-hexane gave 0.23 g of yellow needles.

mp: 60.5°-61.5° C.

Examples 66 to 70

In the same manner as Example 65 and using adequate starting materials, the compounds shown in Table 5 were obtained.

TABLE 5

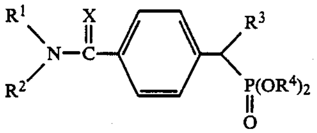

| Example No. | $R^1$ | $R^2$ | $R^3$ | $R^4$ | X | Melting point (°C.) (recrystallization solvent) |
|---|---|---|---|---|---|---|
| 66 | 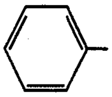 | H | H | $CH_2CH_3$ | S | 175–177 (benzene-n-hexane) |
| 67 | 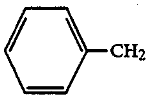 | $CH_3$ | H | $CH_2CH_3$ | S | 1.21(t, J=7.0Hz, 3H), 1.25(t, J=7.0Hz, 3H), 3.00, 3.46(each s, totally 3H), 3.11, 3.14(each d, J=21.8Hz, totally 2H), 3.8–4.2(m, 4H), 4.71, 5.42(each s, totally 2H), 7.0–7.5(m, 9H) |
| 68 | 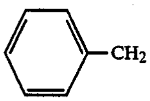 | 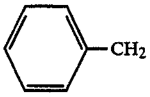 | H | $CH_2CH_3$ | S | 1.19(t, J=7.0Hz, 6H), 3.11(d, J=22.0Hz, 2H), 3.8–4.2(m, 4H), 4.58, 5.37(each s, totally 4H), 6.6–7.4(m, 14H) |
| 69 | 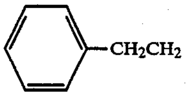 | H | H | 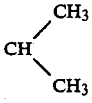 | S | 145–146 (benzene-n-hexane) |
| 70 | 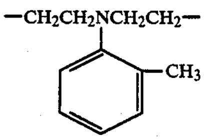 | | H | $CH_2CH_3$ | S | 116.5–118.0 (decomposition) (benzene-n-hexane) |

Examples 71 and 72

In a manner analogous to Example 1, the compounds shown in Table 6 were obtained using appropriate starting materials.

TABLE 6

| Example No. | $R^1$ | $R^2$ | $R^3$ | $R^4$ | X | Melting point (°C.) (recrystallization solvent) |
|---|---|---|---|---|---|---|
| | 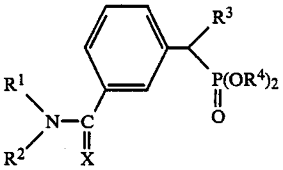 | | | | | |
| 71 | 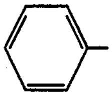 | H | H | $CH_2CH_3$ | O | 103.5–104.5 (benzene-n-hexane) |

TABLE 6-continued

| Example No. | $R^1$ | $R^2$ | $R^3$ | $R^4$ | X | Melting point (°C.) (recrystallization solvent) |
|---|---|---|---|---|---|---|
| | 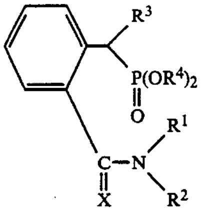 | | | | | |
| 72 | 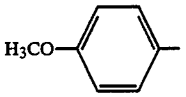 | H | H | $CH_2CH_3$ | O | 1.29(t, 6H, J=7.0Hz), 3.33(d, 2H, J=21.5Hz), 3.80(s, 3H), 3.8-4.3(m, 4H), 6.7-7.9(m, 9H) |

Example 73

In a manner analogous to Example 38, the compound shown in Table 7 was obtained using appropriate starting materials.

TABLE 7

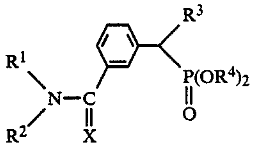

| Example No. | $R^1$ | $R^2$ | $R^3$ | $R^4$ | X | Melting point (°C.) (recrystallization solvent) |
|---|---|---|---|---|---|---|
| 73 | 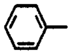 | 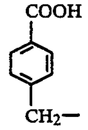 | H | $CH_2CH_3$ | O | 1.20 (t, 6H, J=7.0Hz), 3.06 (d, 2H, J=22.0Hz), 3.7-4.2 (m, 4H), 5.16 (s, 2H), 6.7-8.2 (m, 13H) |

Examples 74 and 75

In a manner analogous to Example 49, the compounds shown in Table 8 were obtained using appropriate starting materials.

TABLE 8

| Example No. | $R^1$ | $R^2$ | $R^3$ | $R^4$ | X | Melting point (°C.) (recrystallization solvent) |
|---|---|---|---|---|---|---|
| | | 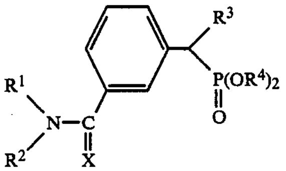 | | | | |
| 74 | 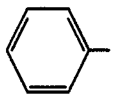 | 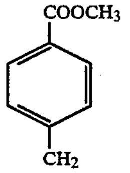 | H | $CH_2CH_3$ | O | 1.20 (t, 6H, J=7.0Hz), 3.20 (d, 2H, J=21.5Hz), 3.7-4.2 (m, 4H), 3.88 (s, 3H), 5.16 (s, 2H), 6.7-8.1 (m, 13H) |
| | | 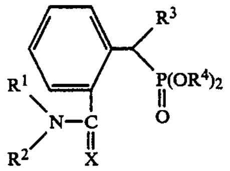 | | | | |

TABLE 8-continued

| Example No. | $R^1$ | $R^2$ | $R^3$ | $R^4$ | X | Melting point (°C.) (recrystallization solvent) |
|---|---|---|---|---|---|---|
| 75 | 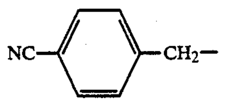 | 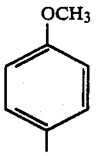 | H | $CH_2CH_3$ | O | 1.28 (t, 6H, J=7.0Hz), 3.52 (d, 2H, J=22.0Hz), 3.65 (s, 3H), 3.8–4.3 (m, 4H), 5.17 (s, 2H), 6.5–7.6 (m, 12H) |

Examples 76 to 83

In a manner analogous to Example 1, the compounds shown in Table 9 were obtained using appropriate starting materials.

TABLE 9

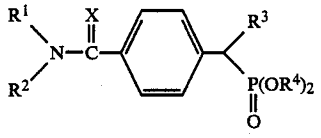

| Example No. | $R^1$ | $R^2$ | $R^3$ | $R^4$ | X | Melting point (°C.) (recrystallization solvent) |
|---|---|---|---|---|---|---|
| 76 | 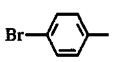 | H | H | $CH_2CH_3$ | O | 133–135 (benzene-n-hexane) |
| 77 | 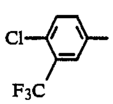 | H | H | $CH_2CH_3$ | O | 188–189 (benzene-n-hexane) |
| 78 | 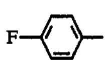 | H | H | $CH_2CH_3$ | O | 147–149 (benzene-n-hexane) |
| 79 | 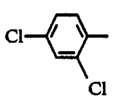 | H | H | $CH_2CH_3$ | O | 136–138 (benzene-n-hexane) |
| 80 | 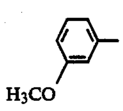 | H | H | $CH_2CH_3$ | O | 108–110 (benzene-n-hexane) |
| 81 | 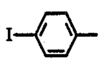 | H | H | $CH_2CH_3$ | O | 141–143 (benzene-n-hexane) |
| 82 | 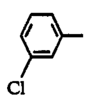 | H | H | $CH_2CH_3$ | O | 141–143 (benzene-n-hexane) |

TABLE 9-continued

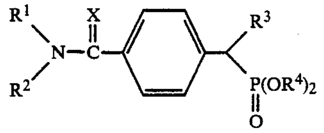

| Example No. | $R^1$ | $R^2$ | $R^3$ | $R^4$ | X | Melting point (°C.) (recrystallization solvent) |
|---|---|---|---|---|---|---|
| 83 | 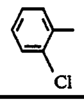 | H | H | $CH_2CH_3$ | O | 122–124 (benzene-n-hexane) |

Examples 84 and 85

In a manner analogous to Example 39, the compounds shown in Table 10 were obtained using appropriate starting materials.

TABLE 10

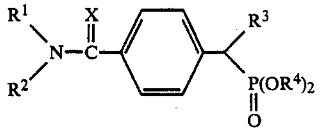

| Example No. | $R^1$ | $R^2$ | $R^3$ | $R^4$ | X | Melting point (°C.) (recrystallization solvent) |
|---|---|---|---|---|---|---|
| 84 | 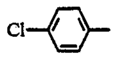 | 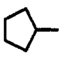 | H | $CH_2CH_3$ | O | 85–88 (benzene-n-hexane) |
| 85 | 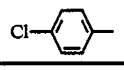 | $CH_3$ | H | $CH_2CH_3$ | O | 79–81 (benzene-n-hexane) |

Examples 86 to 89

In a manner analogous to Example 49, the compounds shown in Table 11 were obtained using appropriate starting materials.

TABLE 11

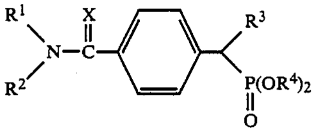

| Example No. | $R^1$ | $R^2$ | $R^3$ | $R^4$ | X | Melting point (°C.) (recrystallization solvent) |
|---|---|---|---|---|---|---|
| 86 | 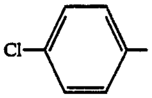 | 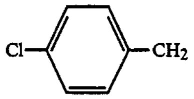 | H | $CH_2CH_3$ | O | 116-118 (benzene-n-hexane) |
| 87 | 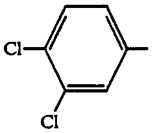 | 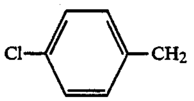 | H | $CH_2CH_3$ | O | 121-123 (benzene-n-hexane) |
| 88 | 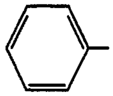 | 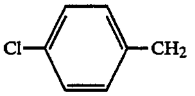 | H | $CH_2CH_3$ | O | 93-95 (benzene-n-hexane) |
| 89 | 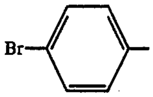 | 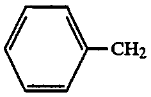 | H | $CH_2CH_3$ | O | 95-97 (benzene-n-hexane) |

(Pharmacological study)

Calcium antagonistic action in vascular smooth muscles

Male Wistar rats weighing about 250 g were anesthetized with ether, hit hard in the occipital region, and the both common carotid arteries were cut to let blood, and the thoracic aorta was removed. Fat tissues depositing on the extracted blood vessel were removed, and a spiral piece of 2 mm×50 mm was prepared.

This spiral piece of aort was kept at 37° C., and was suspended in an organ bath containing $Ca^{2+}$—free Krebs—Henseleit solution ventilated with mixed gas of 95% $O_2$ and 5% $CO_2$ and its contraction reaction was measured in the following method by way of an isotonic transducer.

In the first place, to the spiral piece deprived of $Ca^{2+}$, $CaCl_2$ solution of $10^{-4}$ to $3\times10^{-2}$M was comulatively added in the presence of KCl of $5\times10^{-2}$M, and the dose-reaction curve by $Ca^{2+}$ was determined, and after removing $Ca^{2+}$ again, the dose-reaction curve by $Ca^{2+}$ was determined in the presence of the test compound, and from the difference of these reactions, the $pA_2$ value of $Ca^{2+}$ antagonistic action of the test compound was calculated. The concentration of the test compound was $3\times10^{-7}$ to $10^{-5}$M. (The $pA_2$ value was calculated according to the method proposed by Van Rossum, J. M., in Arch. Int. Pharmarcodyn., 143, 299-330, 1963).

Results obtained from a group of preferable compounds according to this invention are shown in Table 12.

TABLE 12

| Test compound (example No.) | Total samples | $pA_2$ |
|---|---|---|
| 13 | 5 | 6.52 ± 0.10 |
| 45 | 5 | 6.75 ± 0.08 |

TABLE 12-continued

| Test compound (example No.) | Total samples | $pA_2$ |
|---|---|---|
| 46 | 5 | 6.07 ± 0.12 |
| 56 | 5 | 6.99 ± 0.11 |
| 74 | 5 | 6.50 ± 0.09 |

From Table 12 it is evident that the compounds of this invention possess an excellent $Ca^{2+}$ antagonistic action, and they are expected to be useful in the cardiovascular system, in particular, in coronary dilating action and hypotensive action, and they may be used in a wide range as the preparations for the cardiovascular system.

Shown below are examples of prescription of preparations using the compounds of this invention.

Prescription example 1: Preparation of tablets 1,000 tablets for oral use containing 5 mg each of 4-diethoxyphosphinylmethyl-N-benzyl-N-phenylbenzamide are prepared in the following prescription.

| Ingredients | Contents (g) |
|---|---|
| 4-diethoxyphosphinylmethyl-N—benzyl-N—phenylbenzamide | 5 |
| Lactose (conforming to Japanese Pharmacopeia) | 50 |
| Corn starch (conforming to Japanese Pharmacopeia) | 25 |
| Crystalline cellulose (conforming to Japanese Pharmacopeia) | 25 |
| Methyl cellulose (conforming to Japanese Pharmacopeia) | 1.5 |
| Magnesium stearate (conforming to Japanese Pharmacopeia) | 1 |

4-diethoxyphosphinylmethyl-N-benzyl-N-phenylbenzamide, lactose, corn starch, and crystalline cellulose are sufficiently blended, and granulated in 5% aqueous solution of methyl cellulose, and are passes through 200-mesh sieve, and mixed with magnesium stearate, and the mixture is pressed into tablet form.

Prescription example 2: Preparation of capsules 1,000 gelatine capsules for oral use containing 10 mg each of 4-diethoxyphosphinylmethyl-N-benzyl-N-(4-methoxyphenyl)benzamide are prepared in the following prescription.

| Ingredients | Contents (g) |
|---|---|
| 4-diethoxyphosphinylmethyl-N—benzyl-N—(4-methoxyphenyl)benzamide | 10 |
| Lactose (conforming to Japanese Pharmacopeia) | 80 |
| Starch (conforming to Japanese Pharmacopeia) | 30 |
| Talc (conforming to Japanese Pharmacopeia) | 5 |
| Magnesium stearate (conforming to Japanese Pharmacopeia) | 1 |

All ingredients are ground to fine powder, and stirred well until the mixture becomes uniform, and the powder is charged into gelatine capsules for oral use having desired dimensions.

What is claimed is:

1. A carboxamide compound of the formula:

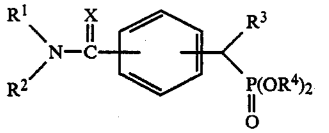

wherein $R^1$ and $R^2$ represent, respectively, a hydrogen atom, an alkyl group, a cycloalkyl group, a diphenyl lower alkyl group, or a group of the formula:

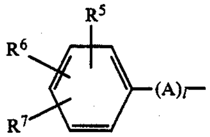

in which $R^5$, $R^6$ and $R^7$ represent, respectively, a hydrogen atom, a halogen atom, a nitro group, a lower alkoxy group, a lower alkoxycarbonyl group, a lower alkyl group, a halogen-substituted lower alkyl group, a cyano group, a carboxy group or a hydroxy group; A represents a lower alkylene group; l represents 0 or 1; or $R^1$ and $R^2$ together with the nitrogen atom to which they are attached form a heterocyclic group or a heterocyclic group containing additional hetero atoms(s) selected from the group consisting of a nitrogen atom and an oxygen atom, or $R^1$ and $R^2$ form said heterocyclic group substituted with a lower alkyl group, a phenyl lower alkyl group, a phenyl group or a phenyl group substituted with a lower alkyl group, a lower alkoxy group, a halogen atom, or a halogen-substituted lower alkyl group as a substituent group; $R^3$ represents a hydrogen atom, an alkyl group, or a phenyl lower alkyl group; $R^4$ represents a lower alkyl group or a phenyl group; and X represents an oxygen atom or a sulfur atom.

2. A carboxamide compound as claimed in claim 1, wherein each of said $R^1$ and $R^2$ represents a hydrogen atom, a $C_1$–$C_8$ alkyl group, or a group of the formula:

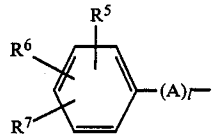

wherein $R^5$, $R^6$, and $R^7$ represent, respectively, a hydrogen atom, a halogen atom, a nitro group, a $C_1$–$C_6$ alkoxy group, a $C_1$–$C_6$ alkoxycarbonyl group, a $C_1$–$C_6$ alkyl group, a $C_1$–$C_6$ alkyl group having 1 to 3 halogen atoms or a cyano group; A represents a $C_1$–$C_6$ alkylene group; and l represents 0 or 1;

$R^3$ represents a hydrogen atom and $R^4$ represents a $C_1$–$C_6$ alkyl group.

3. A carboxamide compound as claimed in claim 2, selected from the group consisting of:

3-diethoxyphosphinylmethyl-N-(4-methoxycarbonylphenyl)-N-phenylbenzamide,
4-diethoxyphosphinylmethyl-N-benzyl-N-phenylbenzamide,
4-diethoxyphosphinylmethyl-N-(2-hydroxyphenyl)-benzamide,
4-diethoxyphosphinylmethyl-N-n-octyl-N-phenylbenzamide,
4-diethoxyphosphinylmethyl-N-benzyl-N-(4-methylphenyl)-benzamide,
4-diethoxyphosphinylmethyl-N-benzyl-N-(4-methoxyphenyl)-benzamide,
4-diethoxyphosphinylmethyl-N-benzyl-N-(3-trifluoromethylphenyl)benzamide,
4-diethoxyphosphinylmethyl-N-benzyl-N-(4-nitrophenyl)-benzamide,
4-diethoxyphosphinylmethyl-N-benzyl-N-(4-cyanophenyl)-benzamide,
4-diethoxyphosphinylmethyl-N-benzyl-N-(3,4-dichlorophenyl)benzamide,
4-diethoxyphosphinylmethyl-N-(4-nitrobenzyl)-N-phenylbenzamide, and
4-diethoxyphosphinylmethyl-N-(4-bromophenyl)-benzamide.

4. A pharmaceutical composition containing a pharmaceutically effective amount, as a calcium antagonistic agent, of the compound as claimed in claim 1 and a pharmaceutically acceptable carrier or diluent.

5. A method of therapeutic treatment of man or animal in need of calcium antagonistic action comprising administering a therapeutically effective amount of the compound as claimed in claim 1.

6. A carboxamide compound as claimed in claim 1, wherein said heterocyclic group formed by $R^1$ and $R^2$ is selected from the group consisting of a pyrrolidinyl group, a piperidono group, a piperazinyl group and a morpholino group.

* * * * *